United States Patent [19]
Dostert et al.

[11] Patent Number: 5,236,957
[45] Date of Patent: Aug. 17, 1993

[54] N-PHENYLALKYL SUBSTITUTED α-AMINO CARBOXAMIDE DERIVATIVES AND PROCESS FOR THEIR PREPARATION

[75] Inventors: Philippe Dostert, Paris, France; Paolo Pevarello, Pavia, Italy; Franco Heidempergher, Parabiago, Italy; Mario Varasi, Milan, Italy; Alberto Bonsignori, Milan, Italy; Romeo Roncucci, Milan, Italy

[73] Assignee: Farmitalia Carlo Erba Srl, Milan, Italy

[21] Appl. No.: 646,596

[22] PCT Filed: May 25, 1990

[86] PCT No.: PCT/EP90/00841

§ 371 Date: Jan. 25, 1991

§ 102(e) Date: Jan. 25, 1991

[87] PCT Pub. No.: WO90/14334

PCT Pub. Date: Nov. 29, 1990

[30] Foreign Application Priority Data

May 25, 1989 [GB] United Kingdom ............... 8912071
Apr. 4, 1990 [GB] United Kingdom ............... 9007567

[51] Int. Cl.$^5$ ............................................. A61K 31/165
[52] U.S. Cl. ................................. 514/620; 514/618; 514/619; 564/162; 564/163; 564/164; 564/165; 564/167; 564/168
[58] Field of Search ............. 564/165, 162, 163, 167, 564/164, 168; 514/620, 357, 438, 471, 618; 546/334, 335; 549/76, 491, 494

[56] References Cited

U.S. PATENT DOCUMENTS

| | | | |
|---|---|---|---|
| 4,049,663 | 9/1977 | Harper et al. | 260/293.86 |
| 4,267,354 | 5/1981 | Krapcho et al. | 560/39 |
| 4,311,853 | 1/1982 | Cree | 562/447 |
| 4,513,009 | 4/1985 | Roques et al. | 514/513 |
| 4,629,468 | 1/1987 | Roncucci et al. | 514/620 |
| 4,631,287 | 12/1986 | Chakraborty et al. | 514/307 |
| 4,715,619 | 2/1988 | Chakraborty et al. | 514/442 |
| 4,728,688 | 3/1988 | Tizzard et al. | 524/504 |
| 4,839,369 | 6/1989 | Youssefyeh et al. | 514/314 |
| 4,927,836 | 5/1990 | Holloway et al. | 514/620 |

FOREIGN PATENT DOCUMENTS 0200101 12/1986 European Pat. Off. .
1140748 1/1969 United Kingdom .

OTHER PUBLICATIONS

*Eur. Neuropsychopharmacol*, 1, pp. 317–319, "New Anticonvulsants with Selective MAO-B Inhibitory Activity", Dostert et al. (Jan. 1991).

*Primary Examiner*—Richard L. Raymond
*Assistant Examiner*—Brian M. Burn
*Attorney, Agent, or Firm*—Oblon, Spivak, McClelland, Maier & Neustadt

[57] ABSTRACT

N-phenylalkyl substituted α-amino carboxamide derivatives of formula (I)

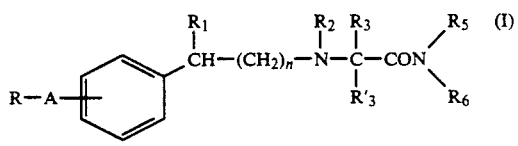

wherein R is $C_1$-$C_8$ alkyl, $C_3$-$C_8$ cycloalkyl, furyl, thienyl, pyridyl or unsubstituted or substituted phenyl; A is a —$(CH_2)_m$— or —$(CH_2)_p$—X—$(CH_2)_q$— group wherein X is —O—, —S— or —$NR_4$—; $R_1$, $R_2$, $R_3$, $R'_3$, $R_4$, n, m, p and q are as herein defined; and each of $R_5$ and $R_6$ is independently hydrogen or $C_1$-$C_6$ alkyl, and the pharmaceutically acceptable salts thereof, are active on the central nervous system and can be used as antiepileptic, anti-Parkinson, neuroprotective, antidepressant, antispastic and/or hypnotic agents in mammals.

15 Claims, No Drawings

N-PHENYLALKYL SUBSTITUTED α-AMINO CARBOXAMIDE DERIVATIVES AND PROCESS FOR THEIR PREPARATION

The present invention relates to N-phenylalkyl substituted α-amino carboxamide derivatives, to their use as therapeutic agents, to a process for their preparation and to pharmaceutical compositions containing them.

Other N-substituted α-amino carboxamide derivatives are known as having pharmacological properties, for instance those described by British patent No. 1140748. The compounds according to this prior art document are useful in the treatment and prophylaxis of such diseases as coronary artery disease and atherosclerosis; moreover they are useful in the treatment of inflammatory conditions such as rheumatoid arthritis.

Further substituted amino acid derivatives are known as enkephalinase inhibitors, analgesics and hypotensives from EP-A-0038758.

Still other substituted glycine and alanine derivatives are disclosed by U.S. Pat. No. 4,049,663. The compounds according to this document have utility as oral analgesics.

It has now been found that N-phenylalkyl substituted α-amino carboxamide derivates of general formula (I), as herein defined, and the pharmaceutically acceptable salts thereof are active as anti-epileptic, anti-Parkinson, neuroprotective, antidepressant, antispastic, and/or hypnotic agents.

Accordingly the present invention relates, as a first object, to the use of a compound of formula (I), as herein defined, or a pharmaceutically acceptable salt thereof, as an antiepileptic, anti-Parkinson, neuroprotective, antidepressant, antispastic, and/or hypnotic agent and to the use of a compound of formula (I), or a pharmaceutically acceptable salt thereof, in the preparation of a pharmaceutical composition for use as an anti-epileptic, anti-Parkinson, neuroprotective, antidepressant, antispastic and/or hypnotic agent.

The compounds of formula (I) have the following general formula:

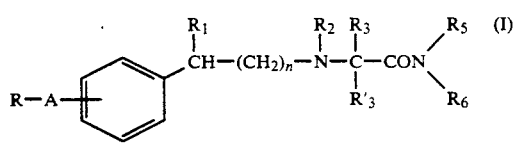

wherein
R is $C_1$-$C_8$ alkyl; a $C_3$-$C_8$ cycloalkyl, furyl, thienyl or pyridyl ring; or a phenyl ring unsubstituted or substituted by 1 to 4 substituents independently chosen from halogen, $C_1$-$C_6$ alkyl, $C_1$-$C_6$ alkoxy and trifluoromethyl;

A is a —$(CH_2)_m$— or —$(CH_2)_p$—X—$(CH_2)_q$— group, wherein m is an integer of 1 to 4, one of p and q is zero and the other is zero or an integer of 1 to 4, and X is —O—, —S— or —$NR_4$— in which $R_4$ is hydrogen or $C_1$-$C_4$ alkyl;

n is zero or 1;

each of $R_1$ and $R_2$, independently, is hydrogen or $C_1$-$C_4$ alkyl;

$R_3$ is hydrogen, $C_1$-$C_4$ alkyl unsubstituted or substituted by hydroxy or by a phenyl ring optionally substituted by 1 to 4 substituents independently chosen from halogen, $C_1$-$C_6$ alkyl, $C_1$-$C_6$ alkoxy and trifluoromethyl;

$R'_3$ is hydrogen; or $R_3$ and $R'_3$ taken together with the adjacent carbon atom form a $C_3$-$C_6$ cycloalkyl ring;

each of $R_5$ and $R_6$, independently, is hydrogen or $C_1$-$C_6$ alkyl; and wherein when R is $C_1$-$C_8$ alkyl, then A is a —$(CH_2)_p$—X—$(CH_2)_q$— group in which p and q are both zero and X is as defined above.

These compounds and their salts are hereafter referred to as the "active compounds" and as the "compounds of the invention". The present invention includes all the possible optical isomers of the compounds of formula (I) and their mixtures, as well as the metabolites of the compounds of formula (I). The present invention also includes within its scope pharmaceutically acceptable bioprecursors and prodrugs of the compounds of formula (I), i.e. compounds, which have a formula different to formula (I), but which nevertheless are directly or indirectly converted in vivo into a compound of formula (I) upon administration to a human being.

Pharmaceutically acceptable salts of the compounds of formula (I) include acid addition salts with inorganic acids, e.g. nitric, hydrochloric, hydrobromic, sulphuric, perchloric, and phosphoric acid, or organic acids, e.g. acetic, propionic, glycolic, lactic, oxalic, malonic, malic, tartaric, citric, benzoic, cinnamic, mandelic, methanesulfonic and salicyclic acids.

The alkyl, alkylamino, alkylthio and alkoxy groups may be branched or straight chain groups. When $R_5$ and $R_6$ are both alkyl groups, the alkyl group for $R_5$ may be same as or different from the alkyl group for $R_6$. A halogen atom is preferably fluorine, chlorine or bromine, in particular fluorine or chlorine.

A $C_1$-$C_8$ alkyl group is preferably a $C_1$-$C_6$ alkyl group.
A $C_1$-$C_6$ alkyl group is preferably a $C_1$-$C_4$ alkyl group.
A $C_1$-$C_4$ alkyl group is e.g. methyl, ethyl, propyl, isopropyl, butyl or tert.butyl, preferably it is methyl or ethyl.

A $C_1$-$C_6$ alkoxy group is e.g. methoxy, ethoxy, propoxy, isopropoxy, butoxy or tert.butoxy, preferably it is methoxy or ethoxy.

A $C_3$-$C_8$ cycloalkyl group is preferably a cyclopentyl, cyclohexyl or cycloheptyl group.

A $C_3$-$C_6$ cycloalkyl ring is preferably a cyclopropyl or cyclopentyl ring.

A thienyl ring is for instance a 2- or 3-thienyl ring.
A pyridyl ring is for instance a 2- or 3- or 4, in particular a 3-pyridyl ring.

A furyl ring is for instance a 2- or 3-furyl ring.
A substituted phenyl ring is preferably substituted by one or two substituents chosen independently from halogen, $C_1$-$C_4$ alkyl and trifluoromethyl.

When in a —$(CH_2)_m$—, —$(CH_2)_p$— or —$(CH_2)_q$— group m, p and/or q is higher than 1, then such group may be a branched or straight alkylene chain. A —$(CH_2)_m$— group is for instance a —$CH(R_{14})$— group in which $R_{14}$ is hydrogen or $C_1$-$C_3$ alkyl, or it is a —$CH_2$—$CH_2$— or —$CH_2$—$CH_2$—$CH_2$— group.

A $C_1$-$C_4$ alkyl group substituted by hydroxy is preferably a hydroxymethyl or 1-hydroxyethyl group.

A $C_1$-$C_4$ alkyl group substituted by a phenyl ring is preferably a benzyl or phenethyl group.

m is preferably 1 or 2.

Each of p and q, being an integer of 1 to 4, it is preferably 1 or 2.

Preferred compounds of the invention are the compounds of formula (I), wherein

R is a phenyl ring unsubstituted or substituted by one or two substituents independently chosen from halogen, $C_1$-$C_4$ alkyl and trifluoromethyl;

A is a —$(CH_2)_m$— or —$(CH_2)_p$—X—$(CH_2)_q$— group, wherein m is 1 or 2, one of p and q is zero and the other is zero, 1 or 2, and X is —O—, —S— or —NH—;

n is zero or 1;

each of $R_1$ and $R_2$, independently, is hydrogen or $C_1$-$C_4$ alkyl;

$R_3$ is hydrogen or $C_1$-$C_4$ alkyl optionally substituted by hydroxy;

$R'_3$ is hydrogen;

each of $R_5$ and $R_6$ is independently hydrogen or $C_1$-$C_4$ alkyl; and the pharmaceutically acceptable salts thereof.

More preferred compounds of the invention are the compounds of formula (I), wherein R is phenyl ring unsubstituted or substituted by halogen;

A is a —$(CH_2)_m$— or —$(CH_2)_p$—X—$(CH_2)_q$— group, wherein m is 1 or 2; one of p and q is zero and the other is zero or 1 and X is —O—, —S— or —NH—;

n is zero;

$R_1$ is hydrogen;

$R_2$ is hydrogen or $C_1$-$C_4$ alkyl;

$R_3$ is hydrogen or $C_1$-$C_2$ alkyl optionally substituted by hydroxy;

$R'_3$ is hydrogen;

each of $R_5$ and $R_6$ independently is hydrogen or $C_1$-$C_4$ alkyl;

and the pharmaceutically acceptable salts thereof.

Examples of particularly preferred compounds of the invention are the following:

2-(4-benzyloxybenzyl)aminopropionamide;
2-[4-(2-chlorobenzyloxy)benzyl]amino-3-hydroxy-N-methylpropionamide;
2-[4-(2-chlorobenzyloxy)benzyl]aminopropionamide;
2-[4-(3-fluorobenzyloxy)benzyl]amino-3-hydroxy-N-methylpropionamide;
2-(4-benzylaminobenzyl)aminopropionamide;
2-[4-(3-fluorobenzyloxy)benzyl]aminopropionamide;
2-[4-(2-fluorobenzyloxy)benzyl]amino-3-hydroxy-N-methylpropionamide;
2-[N-(4-benzylbenzyl)-N-methyl]aminopropionamide;
2-[4-(3-chlorobenzyloxy)benzyl]amino-3-hydroxy-N-methylpropionamide;
2-(4-benzyloxybenzyl)amino-3-hydroxy-N-methylpropionamide;
2-[4-(3-chlorobenzyloxy)benzyl]aminopropionamide;
2-[N-[4-(3-chlorobenzyloxy)benzyl]-N-methyl-]aminoacetamide;
2-[4-(3-chlorobenzyloxy)benzyl]amino-N-methylacetamide;
2-(4-phenyloxybenzyl)amino-3-hydroxy-N-methylproprionamide;
2-(4-benzylbenzyl)aminopropionamide;
2-[4-(2-phenylethyl)benzyl]aminopropionamide;
2-(4-phenyloxymethylbenzyl)aminopropionamide;
2-(4-benzylthiobenzyl)aminopropionamide;
2-[4-(2-chlorobenzyloxy)benzyl]amino-N-methylpropionamide;
2-(4-benzyloxybenzyl)amino-N-methylpropionamide;
2-[4-(3-chlorobenzyloxy)benzyl]aminoacetamide;

if the case, either as single (S) or (R) isomers or as a mixture thereof; and the pharmaceutically acceptable salts thereof. By evaluating the prior art references cited above, it appears clearly that some compounds, falling within the general formula (I) above, are embraced by the general formulae of some of such prior art documents, but therein not specifically mentioned; whereas other compounds of general formula (I) are not covered by the foregoing prior art documents.

A selected class of active compounds of formula (I) are those of formula (Ia)

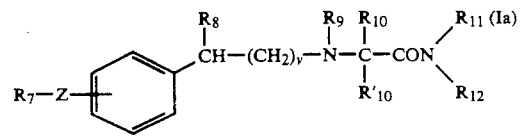

wherein $R_7$ is $C_1$-$C_8$ alkyl; a $C_3$-$C_8$ cycloalkyl, furyl, thienyl or pyridyl ring; or a phenyl ring unsubstituted or substituted by 1 to 4 substituents independently chosen from halogen, $C_1$-$C_6$ alkyl, $C_1$-$C_6$ alkoxy and trifluoromethyl;

Z is a —$(CH_2)_r$— or —$(CH_2)_s$—Y—$(CH_2)_t$— group, wherein r is an integer of 1 to 4, one of s and t is zero and the other is zero or an integer of 1 to 4, and Y is —O—, —S— or —$NR_{13}$— in which $R_{13}$ is hydrogen or $C_1$-$C_4$ alkyl;

v is zero or 1;

each of $R_8$ and $R_9$, independently, is hydrogen or $C_1$-$C_4$ alkyl;

$R_{10}$ is hydrogen, $C_1$-$C_4$ alkyl unsubstituted or substituted by hydroxy or by a phenyl ring optionally substituted by 1 to 4 substituents independently chosen from halogen, $C_1$-$C_6$ alkyl, $C_1$-$C_6$ alkoxy and trifluoromethyl;

$R'_{10}$ is hydrogen; or $R_{10}$ and $R'_{10}$ taken together with the adjacent carbon atom form a $C_3$-$C_6$ cycloalkyl ring;

each of $R_{11}$ and $R_{12}$, independently, is hydrogen or $C_1$-$C_6$ alkyl; and the pharmaceutically acceptable salts thereof; and wherein a) when $R_7$ is $C_1$-$C_8$ alkyl, then Z is a —$(CH_2)_s$—Y—$(CH_2)_t$— group in which both of s and t are zero and Y is as defined above; and wherein b) when $R_7$ is $C_1$-$C_8$ alkyl and, at the same time, Z is a —$(CH_2)_s$—Y—$(CH_2)_t$— group in which both of s and t are zero and Y is —O—, $R_{10}$ is hydrogen or $C_1$-$C_4$ alkyl, $R'_{10}$ is hydrogen, or $R_{10}$ and $R'_{10}$ taken together with the adjacent carbon atom form a $C_3$-$C_6$ cycloalkyl ring and v, $R_9$, $R_{11}$ and $R_{12}$ are as defined above, then $R_8$ is $C_1$-$C_4$ alkyl; and wherein c) when Z is a group —$(CH_2)_s$—Y—$(CH_2)_t$—, in which s, t and Y are as defined above, and at the same time $R_7$ is a furyl, thienyl or pyridyl ring or a phenyl ring unsubstituted or substituted by 1 or 2 substituents chosen from halogen, $C_1$-$C_6$ alkyl, $C_1$-$C_6$ alkoxy and trifluoromethyl, $R_{10}$ is hydrogen or $C_1$-$C_4$ alkyl, $R'_{10}$ is hydrogen, and v, $R_8$ and $R_9$ are as defined above, then at least one of $R_{11}$ and $R_{12}$ is other than hydrogen; and wherein d) when $R_7$ is phenyl unsubstituted or substituted by 1 to 4 substituents chosen from halogen and $C_1$-$C_6$ alkyl, and at the same time Z is a —$CH(R_{14})$— or —$(CH_2)_s$—Y—$(CH_2)_t$— group, in which $R_{14}$ is hydrogen or $C_1$-$C_3$ alkyl, Y is —O— or —S— and s and t are both zero, $R_8$ and $R_9$ are hydrogen, v is zero and $R_{10}$, $R'_{10}$, $R_{11}$ and $R_{12}$ are as defined above, then $R_{10}$ is other than hydrogen or unsubstituted $C_1$-$C_4$ alkyl.

The compounds of general formula (Ia) and their pharmaceutically acceptable salts, which are new, are also an object of the present invention. A further object of the present invention is to provide a pharmaceutical composition containing as active principle a compound of formula (Ia) or a pharmaceutically acceptable salt thereof.

The preferred values of the substituents R, A, $R_1$, $R_2$, $R_3$, $R'_3$, $R_5$ and $R_6$ occurring in formula (I), given above, apply also to the corresponding substituents $R_7$, Z, $R_8$, $R_9$, $R_{10}$, $R'_{10}$, $R_{11}$ and $R_{12}$ occurring in formula (Ia). In particular analogously, when in a —$(CH_2)_r$—, —$(CH_2)_s$— or —$(CH_2)_t$— group r, s and/or t is higher than 1, such group may be a branched or straight alkylene chain. A —$(CH_2)_r$— group is similarly for instance a —$CH(R_{14})$— group in which $R_{14}$ is as defined above or a —$CH_2$—$CH_2$— or —$CH_2$—$CH_2$—$CH_2$— group.

Preferred compounds of formula (Ia), as defined above, are those wherein $R_7$ is a phenyl ring unsubstituted or substituted by one or two substituents independently chosen from halogen, $C_1$-$C_4$ alkyl and trifluoromethyl; Z is a —$(CH_2)_r$— or —$(CH_2)_s$—Y—$(CH_2)_t$ group, wherein r is 1 or 2, one of s and t is zero and the other is zero, 1 or 2, and Y is —O—, —S— or —NH—;

v is zero or 1;

each of $R_8$ and $R_9$, independently, is hydrogen or $C_1$-$C_4$ alkyl;

$R_{10}$ is hydrogen or $C_1$-$C_4$ alkyl optionally substituted by hydroxy; $R'_{10}$ is hydrogen; each of $R_{11}$ and $R_{12}$ is independently hydrogen or $C_1$-$C_4$ alkyl; and the pharmaceutically acceptable salts thereof; and wherein a) when Z is a group —$(CH_2)_s$—Y—$(CH_2)_t$— in which s, t and Y are as defined above and at the same time $R_7$ is a phenyl ring as defined above, $R_{10}$ is hydrogen or unsubstituted $C_1$-$C_4$ alkyl, v, $R_8$ and $R_9$ are as defined above, then at least one of $R_{11}$ and $R_{12}$ is other than hydrogen; and wherein b) when $R_7$ is a phenyl ring unsubstituted or substituted by one or two substituents chosen from halogen and $C_1$-$C_4$ alkyl, and at the same time Z is a —$CH(R_{14})$— or —$(CH_2)_s$—Y—$(CH_2)_t$— group in which $R_{14}$ is hydrogen or $C_1$-$C_3$ alkyl, Y is —O— or —S— and s and t are both zero, $R_8$ and $R_9$ are hydrogen, v is zero and $R_{11}$ and $R_{12}$ are as defined above, then $R_{10}$ is $C_1$-$C_4$ alkyl substituted by hydroxy.

Preferred examples of specific compounds of formula (Ia) are the following:

2-[4-(2-chlorobenzyloxy)benzyl]amino-3-hydroxy-N-methylpropionamide;
2-[4-(3-fluorobenzyloxy)benzyl]amino-3-hydroxy-N-methylpropionamide;
2-[4-(2-fluorobenzyloxy)benzyl]amino-3-hydroxy-N-methylpropionamide;
2-[N-(4-benzylbenzyl)-N-methyl]aminopropionamide;
2-[4-(3-chlorobenzyloxy)benzyl]amino-3-hydroxy-N-methylpropionamide;
2-(4-benzyloxybenzyl)amino-3-hydroxy-N-methylpropionamide;
2-[4-(3-chlorobenzyloxy)benzyl]amino-N-methylacetamide;
2-(4-phenyloxybenzyl)amino-3-hydroxy-N-methylpropionamide;
2-[4-(2-phenylethyl)benzyl]aminopropionamide;
2-[4-(2-chlorobenzyloxy)benzyl]amino-N-methylpropionamide;
2-(4-benzyloxybenzyl)amino-N-methylpropionamide;

if the case, either as single (S) or (R) isomers or as a mixture thereof and the pharmaceutically acceptable salts thereof.

None of the compounds of formula (I) herein specifically mentioned as single chemical entity, but embraced by the general formulae of the prior art documents, has ever been specifically mentioned before in any of them. These new chemical compounds and the pharmaceutically acceptable salts thereof are a further object of the present invention.

Examples of such new compounds are the following:

2-(4-benzyloxybenzyl)aminopropionamide;
2-[4-chlorobenzyloxy)benzyl]aminopropionamide;
2-(4-benzylaminobenzyl)aminopropionamide;
2-[4-(3-fluorobenzyloxy)benzyl]aminopropionamide;
2-[4-(3-chlorobenzyloxy)benzyl]aminoacetamide;
2-[N-[4-(3-chlorobenzyloxy)benzyl]-N-methyl]-aminoacetamide;
2-(4-benzylbenzyl)aminopropionamide;
2-(4-phenyloxymethylbenzyl)aminopropionamide;
2-(4-benzylthiobenzyl))aminopropionamide;

if the case, either as single (S) or (R) isomers or as a mixture thereof and the pharmaceutically acceptable salts thereof.

These new chemical compounds can be represented by the following general formula (Ib)

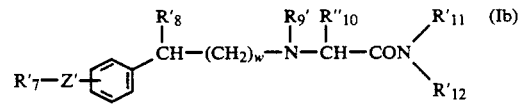

wherein $R'_7$ is a phenyl ring unsubstituted or substituted by a halogen atom;

Z' is a —$(CH_2)_r$— or —$(CH_2)_s$—Y—$(CH_2)_t$— group in which r is 1, one of s and t is zero and the other is zero or 1, and Y is —O— —S— or —NH—

$R'_8$ is hydrogen;

w is zero;

$R'_9$ is hydrogen or methyl;

$R''_{10}$ is hydrogen or methyl;

$R'_{11}$ and $R'_{12}$ are hydrogen.

The compounds of formula (Ib) and the pharmaceutically acceptable salts thereof are a further object of the present invention.

An object according to this invention is also to provide a pharmaceutical composition containing as active principle a compound of formula (Ib) or a pharmaceutically acceptable salt thereof; in particular a compound selected from the group consisting of 2-(4-benzyloxybenzyl)aminopropionamide;
2-[4-(2-chlorobenzyloxy)benzyl]aminopropionamide;
2-(4-benzylaminobenzyl)aminopropionamide;
2-[4-(3-fluorobenzyloxy)benzyl]aminopropionamide;
2-[4-(3-chlorobenzyloxy)benzyl]aminopropionamide;
2-[N-[4-(3-chlorobenzyloxy)benzyl]-N-methyl-]aminoacetamide;
2-[4-(3-chlorobenzyloxy)benzyl]aminoacetamide;
2-(4-benzylbenzyl)aminopropionamide;
2-(4-phenyloxymethylbenzyl)aminopropionamide;
2-(4-benzylthiobenzyl)aminopropionamide;

if the case, either as single (S) or (R) isomers or as a mixture thereof, or a pharmaceutically acceptable salt thereof.

The N-phenylalkyl substituted α-amino carboxamide derivatives of formula (I) can be prepared by the analogy process below. The derivatives of formula (Ia) can be prepared in the same way using starting compounds (IIa) to (IXa), (X) and (XI) in which symbols $R_7$ to $R_{12}$, $R'_{10}$, Z and v replace symbols R, $R_1$ to $R_3$, $R_5$, $R_6$, $R'_3$, A and n respectively in compounds (II) to (IX). The derivatives of formula (Ib) can also be prepared in the same way using starting compounds (IIb) and (IVb) to (IXb), (X) and (XI) in which symbols $R'_7$ to $R'_9$, $R''_{10}$, $R'_{11}$, $R'_{12}$, Z' and w replace symbols R, $R_1$ to $R_3$, $R_5$, $R_6$, A and n respectively in compounds (II) and (IV) to (IX) and the symbol corresponding to $R'_3$ is H. The analogy process for the preparation of the derivatives of formula (I) comprises:

a) reacting a compound of formula (II) or (III), respectively,

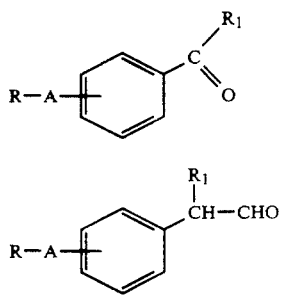

wherein R, $R_1$ and A are as defined above, with a compound of formula (IV)

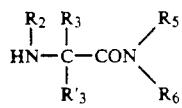

wherein $R_2$, $R_3$ and $R'_3$ are as defined above, and $R_5$ and $R_6$, being as defined above, are not both a $C_1$–$C_6$ alkyl group, thus obtaining a compound of the invention wherein n is zero or 1, respectively, and $R_5$ and $R_6$, being as defined above, are not both $C_1$–$C_6$ alkyl; or b) reacting a compound of formula (V) or an alkyl ester thereof

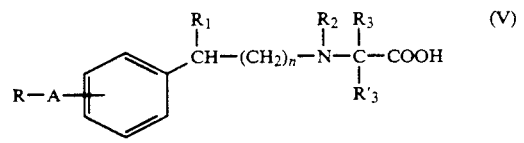

wherein R, A, $R_1$, $R_2$, $R_3$, $R'_3$ and n are as defined above, with an amine of formula (VI)

wherein $R_5$ and $R_6$ are as defined above; or c) reacting a compound of formula (VII)

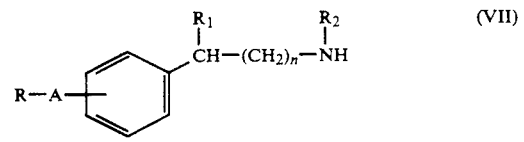

wherein R, A, $R_1$, n and $R_2$ are as defined above, with a compound of formula (VIII)

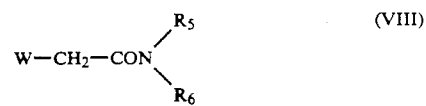

wherein W is a halogen atom and $R_5$ and $R_6$ are as defined above; thus obtaining a compound of the invention wherein $R_3$ and $R'_3$ are both hydrogen; or d) reacting a compound of formula (IX)

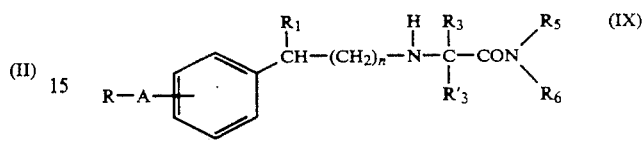

wherein R, A, $R_1$, n, $R_3$, $R'_3$, $R_5$ and $R_6$ are as defined above, with a compound of formula (X) or (XI)

wherein W is a halogen atom; $R''_9$ is $C_1$–$C_4$ alkyl and $R'''_9$ is hydrogen or $C_1$–$C_3$ alkyl, thus obtaining a compound of the invention in which $R_2$ is $C_1$–$C_4$ alkyl; and, if desired, converting a compound of the invention into another compound of the invention and/or, if desired, converting a compound of the invention into a pharmaceutiacally acceptable salt and/or, if desired, converting a salt into a free compound and/or, if desired, separating a mixture of isomers of compounds of the invention into the single isomers.

All the processes described hereabove are analogy processes and can be carried out according to well known methods in organic chemistry.

The reaction of a compound of formula (II) or (III) with a compound of formula (IV) is a reductive amination reaction which can be carried out according to well known methods. According to a preferred embodiment of the invention it may be performed under nitrogen atmosphere, in a suitable organic solvent, such as an alcohol, e.g. a lower alkanol, in particular methanol, or in acetonitrile, at a temperature ranging from about 0° C. to about 40° C., in the presence of a reducing agent, the most appropriate being sodium cyanoborohydride. Occasionally molecular sieves can be added to the reaction mixture for facilitating the reaction.

An alkyl ester of a compound of formula (V) is e.g. a $C_1$–$C_6$ alkyl ester such as a $C_1$–$C_4$ alkyl ester and, in particular a methyl, ethyl or propyl ester, which may be unsubstituted or substituted by a phenyl ring optionally substituted by a nitro group.

Preferably an alkyl ester of a compound of formula (V) is used.

The reaction of a compound of general formula (V) or of an alkyl ester thereof, with an amine of formula (VI) can be performed using an excess of the amine, eventually in the presence of water or of an organic solvent, such as dimethylformamide. The temperature of the reaction may range from about 20° C. to about 100° C.

In a compound of formula (VIII) W is preferably bromine or chlorine. The reaction of a compound of general formula (VII) with a compound of general formula (VIII) can be carried out in a suitable organic solvent, such as an alcohol, e.g. ethanol, or in dimethylformamide, at a temperature ranging from about 40° C. to about 140° C. in the presence of a suitable acid acceptor e.g. anhydrous potassium carbonate.

In a compound of formula (X) the halogen W is preferably iodine. The alkylation reaction of a compound formula (IX) with a compound of formula (X) can be carried out in a suitable organic solvent, such as an alcohol, e.g. methanol, ethanol or isopropanol, in particular in methanol, at a temperature ranging from about 0° C. to about 50° C.

The alkylation reaction of a compound of formula (IX) with an aldehyde of formula (XI) can be carried out in a suitable organic solvent, such as an alcohol, e.g. methanol, or acetonitrile in the presence of a suitable reducing agent, such as sodium cyanoborohydride, at a temperature ranging from about 0° C. to about 30° C.

A compound of the invention can be converted, as stated above, into another compound of the invention by known methods. Process-variant d) above may be regarded as an example of optional conversion of a compound of the invention into another compound of the invention.

Also the optional salification of a compound of the invention as well as the conversion of a salt into the free compound and the separation of a mixture of isomers into the single isomers may be carried out by conventional methods.

The compounds of formulae (II), (III), (IV), (V), (VI), (VII), (VIII), (X) and (XI) are known compounds or can be obtained by known methods from known compounds.

For instance, the carboxylic acids of formula (V) and the alkyl esters thereof can be obtained as described in GB-A-1140748 (Derwent 30027F). An acid of formula (V), in which n is zero or 1, can be obtained also by reacting a compound of formula (II) or (III), respectively, as defined above, with a compound of formula (XII)

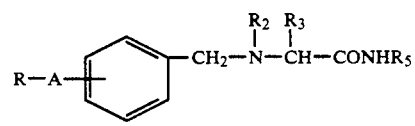

wherein $R_2$, $R_3$ and $R'_3$ are as defined above.

The reaction of a compound of formula (XII) with a compound of formula (II) or (III) may be carried out by following the same procedure previously described as to process-variant a). The compounds of formula (IX) are compounds according to the present invention wherein $R_2$ is hydrogen and can be obtained by process variants a) and b) herein described.

The compounds of formula (XII) are known compounds or can be obtained by known methods.

When in the compounds of the present invention and in the intermediate-products thereof, groups are present, which need to be protected before submitting them to the hereabove illustrated reactions, they may be protected before being reacted and then deprotected, according to methods well known in organic chemistry.

The intermediate compounds, according to the processes herein described for the preparation of the compounds of the invention, may be either in the form of a single isomer or as a mixture thereof. Preferably they are in the form of a single isomer.

Pharmacology

The compounds of the invention and the selected classes thereof of formula (Ia) and (Ib), as herein defined, are active on the central nervous system (CNS) and can be used in therapy, for example as antiepileptics, in the treatment of Parkinson's disease and as neuroprotective agents in degenerative processes associated with normal ageing or pathological situations, such as brain ischemia; they can also be used as antidepressants, hypnotics and antispastic agents.

The activity on the CNS of the compounds of the invention was evaluated on the basis of pharmacological methods, such as, for example, the antagonism of convulsions and lethality induced by intravenous injection of bicucculine in mice (Antiepileptic Drug, D. M. Woodbury et al. eds., 2nd edition, Raven Press, New York, 1982), or the antagonism of convulsions induced in mice by subcutaneous injection of 3-mercaptopropionic acid (W. Löscher, Biochem. Pharmacol., 28; 1397–1407, 1979). Accordingly in following Tables 1 and 2, the doses which protect 50% of the mice (i.e. $ED_{50}$) from lethality and tonic convulsions induced by bicucculine and 3-mercaptopropanoic acid, respectively, are given for a representative group of compounds according to the present invention.

TABLE 1

Antagonism of bicucculine-induced lethality in mice.
Drugs were given orally 1 h before bicucculine (0.6 mg/kg, i.v.)

| Internal code (FCE) | R—A— | $R_2$ | $R_3$ | $R_5$ | * | $ED_{50}$ mg/kg, p.o. |
|---|---|---|---|---|---|---|
| 25989 | m. chlorobenzyloxy | H | H | H | | 190 |
| 26312 | m. chlorobenzyloxy | H | $CH_3$ | H | R | 50 |
| 26358 | benzyloxy | H | $CH_2OH$ | $CH_3$ | S | 16 |
| 26359 | m. chlorobenzyloxy | H | $CH_2OH$ | $CH_3$ | S | 29 |
| 26502 | o. chlorobenzyloxy | H | $CH_2OH$ | $CH_3$ | S | 27 |
| 26550 | benzyloxy | H | $CH_3$ | H | S | 15 |
| 26649 | o. fluorobenzyloxy | H | $CH_2OH$ | $CH_3$ | S | 12 |
| 26650 | m. fluorobenzyloxy | H | $CH_2OH$ | $CH_3$ | S | 25 |
| 26700 | o. chlorobenzyloxy | H | $CH_3$ | H | S | 17 |
| 26723 | benzyl | H | $CH_3$ | H | S | 16 |
| 26743 | m. fluorobenzyloxy | H | $CH_3$ | H | S | 29 |
| 26749 | benzylamino | H | $CH_3$ | H | S | 9 |
| 26762 | benzyl | $CH_3$ | $CH_3$ | H | S | 54 |
| Valproate | | | | | | 401 |

*absolute configuration

TABLE 2

Antagonism of 3-mercaptopropionic acid (MPA) induced tonic convulsions in mice; drugs were given orally 1 h before MPA (60 mg/kg s.c.)

| Internal code | $ED_{50}$ (mg/kg, p.o.) |
|---|---|
| FCE 25989 | 28 |
| FCE 26312 | 10 |
| FCE 26358 | 43 |
| FCE 26359 | 29 |
| FCE 26502 | 16 |
| FCE 26550 | 13 |
| Valproate | 302 |

The $ED_{50}$ data set out in tables 1 and 2 show that the compounds according to the present invention are very active as antiepileptic agents. In fact $ED_{50}$ values largely higher than those determined for the compounds of the invention were found with Valproate, which is a very well known and largely used antiepileptic drug.

The internal FCE codes occurring in Tables 1 and 2 identify the following compounds (enclosed in brackets is the internal FCE code):

[25989] 2-[4-(3-chlorobenzyloxy)benzyl]aminoacetamide;
[26550] (S)-2-(4-benzyloxybenzyl)aminopropionamide;
[26502] (S)-2-[4-(2-chlorobenzyloxy)benzyl]amino-3-hydroxy-N-methylpropionamide;
[26700] (S)-2-[4-(2-chlorobenzyloxy)benzyl]aminopropionamide;
[26650] (S)-2-[4-(3-fluorobenzyloxy)benzyl]amino-3-hydroxy-N-methylpropionamide;
[26749] (S)-2-(4-benzylaminobenzyl)aminopropionamide;
[26743] (S)-2-[4-(3-fluorobenzyloxy)benzyl]aminopropionamide;
[26649] (S)-2-[4-2-fluorobenzyloxy)benzyl]amino-3-hydroxy-N-methylpropionamide;
[26762] (S)-2-[N-(4-benzylbenzyl)-N-methyl]aminopropionamide;
[26359] (S)-2-[4-(3-chlorobenzyloxy)benzyl]amino-3-hydroxy-N-methylpropionamide;
[26358] (S)-2-(4-benzyloxybenzyl)amino-3-hydroxy-N-methylpropionamide;
[26312] (R)-2-[4-(3-chlorobenzyloxy)benzyl]aminopropionamide; and
[26723] (S)-2-(4-benzylbenzyl)aminopropionamide.

The compounds of the invention are also potent inhibitors of monoamine oxidase (MAO). As an example, using rat liver mitochondria as the source of MAO and 2-phenylethylamine as substrate, a $IC_{50}$ value of $2 \times 10^{-7}$M toward MAO type B was found for compound FCE 25989. The activity of brain MAO-B has been shown to be increased with ageing as well as in degenerative disorders (for review, see M. Strolin Benedetti and P. Dostert, Biochem. Pharmacol. 38: 555–561, 1988). The compounds of the invention have also been shown to increase the levels of serotonin (5-HT) and of its main metabolite, 5-hydroxy-indole-3-acetic acid (5-HIAA) in various brain areas. As an example, administration (200 mg/kg; p.o.) of compound FCE 25989 to mice was found to result in an increase of 5-HT (48%) and 5-HIAA (37%) in frontal cortex. Administration of L-tryptophan, the natural bioprecursor of 5-HT and 5-HIAA has been shown to be effective in the treatment of affective disorders and mild to moderate insomnia (for review, see B. Boman, Aust. New Zealand J Psychiatry 22: 83–97, 1988).

The toxicity of the compounds of the invention is negligible; therefore they can be safely used in therapy. The toxicity was evaluated as follows: nine hours food deprived mice were treated orally with single administration of increasing doses, then housed and normally fed. The orientative acute toxicity ($LD_{50}$) was assessed on the senventh day after the treatment.

The compounds of the invention can be administered in a variety of dosage forms, e.g. orally, in the form of tablets, capsules, sugar or film coated tablets, liquid solutions; rectally, in the form of suppositories; parenterally, e.g. intramuscularly or by intravenous injection or infusion. The therapeutic regimen for the different clinical syndromes must be adapted to the type of pathology taking into account as usual, also the route of administration, the form in which the compound is administered and the age, weight and conditions of the subject involved.

The oral route is employed, in general, for all conditions requiring such compounds. In emergency situations preference is given to intravenous injection.

For these purposes the compounds of the invention can be administered orally at doses ranging e.g. from about 50 to about 1500 mg/day. Of course, these dosage regimens may be adjusted to provide the optimal therapeutic response. The nature of the pharmaceutical compositions containing the compounds of this invention in association with pharmaceutically acceptable carriers or diluents will, of course, depend upon the desired route of administration.

The compositions may be formulated in the conventional manner with the usual ingredients. For example, the compounds of the invention may be administered in the form of aqueous or oily solutions or suspensions, tablets, pills, gelatine capsules, syrups, drops or suppositories.

Thus, for oral administration, the pharmaceutical compositions containing the compounds of this invention are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injection or infusion may contain as carrier, for example, sterile water or preferably they may be in the form of sterile aqueous isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

22.4 g (0.203 mol) of glycinamide hydrochloride are suspended in 1000 ml of dry methanol and 10.2 g (0.162 mol) of sodium cyanoborohydride are added while stirring under nitrogen. After solubilization of the mixture, 50 g (0.203 mol) of 3-chlorobenzyloxybenzaldehyde are added in a single portion. The reaction mixture is stirred 8 hours at room temperature and then allowed to stand 16 hours. The solution is filtered and evaporated, taken up with water and extracted three times with methylene chloride. After drying and evaporating, the crude residue is chromatographed on silica gel (eluant: chloroform/methanol/conc. NH4OH; 97/3/0.3) to give 2-[4-(3-chlorobenzyl)oxybenzyl] aminoacetamide which by reaction with the stoichiometric amount of gaseous HCl in ethanol is transformed into its hydrochloride (32.1 g, 46.3%, m.p.: 225°–230° C.).

Analogously, the following compounds can be obtained, starting from the corresponding aldehyde or ketone and the appropriate α-aminoamide and, if the case, a suitable acidic agent:

(4-Benzyloxybenzyl)aminoacetamide, hydrochloride, m.p. 250° C.;
[4-(3-chlorobenzyloxy)-α-methyl-benzyl]aminoacetamide, hydrochloride, m.p. 199.5°–202° C.;
(R)-2-[4-(3-Chlorobenzyloxy)benzyl]amino-3-hydroxy-propionamide, m.p. 110°–110.5° C.;
(S)-2-[4-(3-Chlorobenzyloxy)benzyl]amino-3-hydroxy-propionamide, m.p. 111°–113° C.;
2-[4-(3-Chlorobenzyloxy)benzyl]amino-N-methylacetamide, hydrochloride, m.p. 226°–228° C.;
(S)-2-[4-(3-Chlorobenzyloxy)benzyl]amino-N-methyl-propionamide, hydrochloride; m.p. 176.5°–178.5° C.;
(S)-2-[4-(3-Chlorobenzyloxy)benzyl]amino-3-hydroxy-N-methyl propionamide, m.p. 128°–130° C.;
(S)-2-[4-(3-Chlorobenzyloxy)benzyl]aminopropionamide, m.p. 198.5° C.;
(S)-2-(4-Benzyloxybenzyl)amino-N-methylpropionamide, m.p. 189°–191.5° C.
(S)-2-(4-Benzyloxybenzyl)amino-3-hydroxy-N-methyl-propionamide, m.p. 102°–104° C.;
(R)-2-[4-(3-Chlorobenzyloxy)benzyl]aminopropionamide, hydrochloride m.p. 198.5°–200° C.;
(R)-2-(4-Benzyloxybenzyl)amino-3-hydroxy-N-methyl-propionamide, m.p. 100°–103° C.;
(S)-2-[4-(3-Methoxybenzyloxy)benzyl]amino-3-hydroxy-N-methyl propionamide, m.p. 83°–87° C.;
(S)-2-[4-(2-Chlorobenzyloxy)benzyl]amino-3-hydroxy-N-methyl propionamide, m.p. 131°–134° C.;
(S)-2-[4-(4-Chlorobenzyloxy)benzyl]amino-3-hydroxy-N-methyl propionamide, m.p. 139°–141° C.;
1-[(4-Benzyloxybenzyl)amino]cyclopentane-1-N-methylcarboxamide, hydrochloride, m.p. 218°–221° C.;
2-(4-Benzyloxybenzyl)amino-N-methylacetamide, hydrochloride, m.p. 238°–242° C.
1-[(4-Benzyloxybenzyl)amino]cyclopropane-1-N-methylcarboxamide, hydrochloride, m.p. 194–200 (dec) °C.;
1-[(4-Benzyloxybenzyl)amino]cyclopentane-1-carboxamide, hydrochloride, m.p. 229°–234° C.;
(S)-2-(4-Benzyloxybenzyl)aminopropionamide, m.p. 229°–232° C.;
(S)-2-(4-Benzyloxybenzyl)amino-3-methyl-N-methyl-butanamide, hydrochloride, m.p. 160°–163° C.;
(R)-2-(4-Benzyloxybenzyl)amino-3-methyl-N-methyl-butanamide, hydrochloride, m.p. 161°–165° C.;
(R)-2-(4-Benzyloxybenzyl)amino-3-phenyl-N-methyl-propionamide, m.p. 222.5°–227.5° C.;
1-[(4-Benzyloxybenzyl)amino]cyclopropane-1-carboxamide, methanesulfonate, m.p. 219–228 (dec) °C.;
(R)-2-(4-Benzyloxybenzyl)aminopropionamide, hydrochloride, m.p. 228°–231° C.;
(2R,3S)-2-(4-Benzyloxybenzyl)amino-3-hydroxy-N-methylbutanamide, hydrochloride, m.p. 187.5°–191° C.;
(2S,3R)-2-(4-Benzyloxybenzyl)amino-3-hydroxy-N-methylbutanamide, hydrochloride, m.p. 187°–191° C.;
(S)-2-(4-Benzyloxybenzyl)amino-4-methyl-N-methyl-pentanamide, hydrochloride, m.p. 141°–144° C.;
(S)-2-(4-Benzyloxybenzyl)amino-3-hydroxy-propionamide, m.p. 128.5°–130° C.;
(R)-2-(4-Benzyloxybenzyl)amino-3-hydroxy-propionamide, m.p. 117°–122° C.;
(S)-2-[4-(2-Methylbenzyloxy)benzyl]amino-3-hydroxy-N-methyl propionamide, methanesulfonate, m.p. 170°–172° C.;
(S)-2-[4-(3-Methylbenzyloxy)benzyl]amino-3-hydroxy-N-methyl propionamide, methanesulfonate, m.p. 80°–82° C. (water 0.57%);
(S)-2-[4-(3-Trifluoromethylbenzyloxy)benzyl]amino-3-hydroxy-N-methylpropionamide, methanesulfonate, m.p. 120.5°–124° C.;
(S)-2-[4-(2-Trifluoromethylbenzyloxy)benzyl]amino-3-hydroxy-N-methylpropionamide, methanesulfonate, m.p. 60°–70° C. (water 1.39%);
(S)-2-[4-(2-Fluorobenzyloxy)benzyl]amino-3-hydroxy-N-methylpropionamide, methanesulfonate, m.p. 137°–140° C.;
(S)-2-[4-(3-Fluorobenzyloxy)benzyl]amino-3-hydroxy-N-methylpropionamide, methanesulfonate, m.p. 135°–138° C.;
(S)-2-[4-(2-Chlorobenzyloxy)benzyl]aminopropionamide, methanesulfonate, m.p. 219°–220° C.;
(S)-2-[4-(2-Chlorobenzyloxy)benzyl]amino-N-methylpropionamide, methanesulfonate, m.p. 80°–90° (water 1.21%) °C.;
(R)-2-[4-(2-Chlorobenzyloxy)benzyl]amino-N-methylpropionamide, methanesulfonate, m.p. 130°–134° C.;
(R)-2-[4-(2-Chlorobenzyloxy)benzyl]aminopropionamide, methanesulfonate, m.p. 218°–221° C.;
(R)-2-(4-Benzyloxybenzyl)amino-N-methylpropionamide, methanesulfonate, m.p. 134.5°–138.5° C.;
(S)-2-(4-Phenyloxybenzyl)aminopropionamide, methanesulfonate, m.p. 210°–213° C.;
(S)-2-(4-Phenyloxybenzyl)amino-3-hydroxy-N-methyl propionamide, methanesulfonate, m.p. 112°–116° C.;
(S)-2-(4-Benzylbenzyl)aminopropionamide, methanesulfonate, m.p. 182°–185° C.;
(S)-2-[4-(2-phenylethyl)benzyl]aminopropionamide, methanesulfonate, m.p. 235°–238° C.;
(S)-2-(4-Benzylbenzyl)amino-3-hydroxy-N-methylpropionamide, methanesulfonate, m.p. 126°–128° C.;
(S)-2-(4-Phenylethyloxybenzyl)aminopropionamide, methanesulfonate, m.p. 178°–181° C.;
(S)-2-(4-Benzylthiobenzyl)aminopropionamide, methanesulfonate, m.p. 250° C.;
(S)-2-(4-Benzylthiobenzyl)amino-3-hydroxy-N-methylpropionamide, methanesulfonate, m.p. 151°–155° C.;
(S)-2-(4-Phenylethylbenzyl)amino-3-hydroxy-N-methylpropionamide, methanesulfonate, m.p. 143°–146° C.;
(S)-2-[4-(2-Phenylethyloxy)benzyl]amino-3-hydroxy-N-methylpropionamide, methanesulfonate, m.p. 108°–110° C.;
(S)-2-(4-Phenyloxymethylbenzyl)aminopropionamide, methanesulfonate, m.p. 212°–217° C.;

(S)-2-[4-(2-Fluorobenzyloxy)benzyl]aminopropionamide, m.p. 237°-241° C.;

(S)-2-[4-(3-Fluorobenzyloxy)benzyl]aminopropionamide, m.p. 208°-212° C.;

(S)-(+)-2-(4-Phenyloxymethylbenzyl)amino-3-hydroxy-N-methylpropionamide, methanesulfonate, m.p. 125°-128° C.;

(S)-2-(4-Benzylaminobenzyl)amino-3-hydroxy-N-methylpropionamide, dihydrochloride m.p. 193°-195° C.;

(S)-2-(4-Benzylaminobenzyl)aminopropionamide, dihydrochloride m.p. 173° C.;

(S)-2-(4-Benzyloxyphenetyl)aminopropionamide, methanesulfonate;

(S)-2-[4-(2-Chlorobenzyloxy)phenetyl]aminopropionamide, methanesulfonate;

2-[4-(3-Chlorobenzyloxy)-α-methyl-benzyl]aminopropionamide, methanesulfonate;

(S)-2-[4-(3-Phenylpropyloxy)benzyl]aminopropionamide, methanesulfonate;

2-[(4-Benzyl)-α-methyl-benzyl]aminopropionamide, methanesulfonate;

(R)-2-(4-Benzyloxybenzyl)aminobutanamide, methanesulfonate;

(S)-2-(4-Benzyloxybenzyl)aminobutanamide, methanesulfonate;

(S)-2-(2-Benzyloxybenzyl)aminopropionamide, methanesulfonate;

(S)-2-(3-Benzyloxybenzyl)aminopropionamide, methanesulfonate;

(S)-2-(4-Cyclohexylmethylaminobenzyl)aminopropionamide, dihydrochloride;

(S)-2-(4-Cyclopropylmethylaminobenzyl)aminopropionamide, dihydrochloride;

(S)-2-(4-Phenylaminomethylbenzyl)aminopropionamide, dihydrochloride;

(S)-2-(4-Benzylaminomethylbenzyl)aminopropionamide, dihydrochloride;

(S)-2-[4-(3-Furfuryloxy)benzyl]aminopropionamide, methanesulfonate;

(S)-2-[4-(2-Furfuryloxy)benzyl]aminopropionamide, methanesulfonate;

(S)-2-[4-(3-Pyridyl)methyloxybenzyl]aminopropionamide, methanesulfonate;

(S)-2-[4-(2-Pyridyl)methyloxybenzyl]aminopropionamide, methanesulfonate;

(S)-2-[4-(4-Pyridyl)methyloxybenzyl]aminopropionamide, methanesulfonate;

(S)-2-[4-(3-Thenyloxy)benzyl]aminopropionamide, methanesulfonate; and (S)-2-[4-(2-Thenyloxy)benzyl]aminopropionamide, methanesulfonate.

EXAMPLE 2

0.8 g (0.00298 mol) of (S)-(+)-2-(4-benzylbenzyl)aminopropionamide are dissolved in 45 ml of acetonitrile under a nitrogen stream. To this mixture, 2.98 ml (0.0149 mol) of 37% formaldehyde and 0.27 g (0.00432 mol) of sodium cyanoborohydride are added at room temperature. After 40 min glacial acetic acid is dropped up to neutrality of the solution. The mixture is evaporated to dryness and 40 ml of 2N KOH are added. After extracting with ethyl acetate, washing with N/2 KOH and then with water and brine, the solution is dried on Na2SO4, then filtered and evaporated to obtain a crude oil which is chromatographed on silica gel (eluant CHCl3/MeOH/conc. NH4OH; 200/3/0.2) to give 0.58 g (69%) of a colourless oil. The product is dissolved in methanol and reacted with an equimolar quantity of oxalic acid, to obtain white crystals of (S)-2-[N-(4-benzylbenzyl)-N-methyl]aminopropionamide, oxalate (m.p. 58°-64° C.).

Analogously the following compounds can be obtained, starting from the corresponding secondary amine:

(R)-2-[N-(4-Benzyloxybenzyl)-N-methyl]amino-3-hydroxy-N-methyl propionamide, m.p. 73°-77° C.;

(S)-2-[N-(4-Phenyloxymethylbenzyl)-N-methyl]aminopropionamide;

(S)-2-[N-(4-Benzylethylbenzyl)-N-methyl]aminopropionamide;

(S)-2-[N-(4-Benzylbenzyl)-N-methyl)]amino-3-hydroxy-N-methylpropionamide;

(S)-2-[N-(4-Benzylthiobenzyl)-N-methyl]aminopropionamide;

(S)-2-[N-(4-Benzylaminobenzyl)-N-methyl]aminopropionamide; (NMR;δ(CDCl3):1.05 (d,3H,Me) 2.02 (s,3H,N-Me) 3.55 (q,1H,CH—CONH2) 4.20 (s,2H,ArCH2NMe) 4.28 (s,2H,ArCH2NHAr) 6.55-7.30 (m,11H,arom.+CONH2);

(S)-2-[N-(4-(2-Chlorobenzyloxy)benzyl)-N-methyl]amino-3-hydroxy-N-methylpropionamide, methanesulfonate;

(S)-2-[N-(4-(3-Fluorobenzyloxy)benzyl)-N-methyl]amino-3-hydroxy-N-methylpropionamide, methanesulfonate;

(S)-2-[N-(4-(2-Fluorobenzyloxy)benzyl)-N-methyl]amino-3-hydroxy-N-methylpropionamide, methanesulfonate;

(S)-2-[N-(4-(3-Fluorobenzyloxy)benzyl)-N-methyl]aminopropionamide, methanesulfonate; and (S)-2-[N-(4-(2-Chlorobenzyloxy)benzyl)-N-methyl]amino propionamide, methanesulfonate.

EXAMPLE 3

33.5 g (0.149 mol) of N-benzylidene-tyramine are added to a mixture of 4.45 g (0.193 mol) of sodium in 400 ml of anhydrous ethanol. After cooling to 0°-5° C., a solution of 3-chlorobenzylchloride (28.8 g; 0.193 mol) in dry ethanol (150 ml) is dropped. After stirring 1 hour at room temperature, reflux is maintained for 6 hours. The hot mixture is filtered and the solution is concentrated to dryness. The residue is taken up with 10% HCl (170 ml) and heated at 70°-75° C. for 1 hour. The white solid precipitate is filtered and washed with n-hexane. After recrystallization from ethanol, 31 g of 4-(3-chlorobenzyloxy)phenetylamine,hydrochloride are obtained, m.p. 195-200 (dec).

31 g (0.104 mol) of 4-(3-chlorobenzyloxy)phenetylamine hydrochloride are suspended in 450 ml of anhydrous ethanol. To this mixture, 9.7 g (0.104 mol) of chloroacetamide and 28.8 g (0.208 mol) of anhydrous potassium carbonate are added. After heating to reflux, stirring is continued for 40 hours. The hot mixture is filtered, then evaporated to dryness and the crude residue chromatographed on silica gel (eluant CHCl3/MeOH/conc. NH4OH; 97/3/0.3). The free compound obtained (20.2 g; 60.7%) is treated with gaseous HCl in ethanol to give a quantitative yield of the corresponding [4-(3-chlorobenzyloxy)phenetyl]aminoacetamide, hydrochloride, m.p. 248°-251° C.

Analogously the following compound can be obtained, starting from the corresponding primary amine:

[4-(3-chlorobenzyloxy)-α-methyl-benzyl]aminoacetamide, hydrochloride, m.p. 199.5°-202° C.;

2-[(4-Benzylphenylethyl]aminoacetamide; and

2-[2-(4-Benzylamino)phenylethyl]aminoacetamide;

EXAMPLE 4

7.07 g (0.066 mol) of glycine ethyl ester, hydrochloride are diluted in 200 ml of dry methanol and 3.32 g (0.053 mol) of sodium cyanoborohydride are added, while stirring under nitrogen. To this solution, 15 g (0.0608 mol) of 3-chlorobenzyloxybenzaldehyde are added in a single portion. Stirring is continued for 18 hours at room temperature, the mixture is evaporated to dryness and the crude residue chromatographed on silica gel (eluant: cyclohexane/ethyl acetate; 60/40). 6.8 g (34%) of [4-(3-chlorobenzyloxy)benzyl]amino acetic acid, ethyl ester are obtained (m.p. 114°-115° C. as hydrochloride). 3 g (0.0090 mol) of the above ester (free base) are heated in 70 ml of dimethylamine at 60° C. for 7 hours. The solution is allowed to stand overnight at room temperature, then evaporated and the residue is purified on silica gel (eluant: chloroform/methanol/30% NH4OH; 95/5/0.5) to afford 0.7 g (23%) of [4-(3-chlorobenzyloxy)benzyl]amino-N,N-dimethylacetamide, hydrochloride (m.p. 120°-125° C.).
Analogously the following compounds can be obtained, starting from the corresponding ethyl esters:
2-(4-Benzyloxybenzyl)amino-N,N-dimethylacetamide;
2-(4-Benzyloxybenzyl)amino-3-hydroxy-N,N-dimethylpropionamide;
2-(4-Benzylbenzyl)amino-N,N-dimethylacetamide
2-(4-Benzylaminobenzyl)amino-N,N-dimethylacetamide;
(S)-2-[4-(2-Chlorobenzyloxy)benzyl]amino-3-hydroxy-N,N-dimethylpropionamide, methanesulfonate;
(S)-2-[4-(3-Fluorobenzyloxy)benzyl]amino-3-hydroxy-N,N-dimethylpropionamide, methanesulfonate;
(S)-2-[4-(2-Fluorobenzyloxy)benzyl]amino-3-hydroxy-N,N-dimethylpropionamide, methanesulfonate;
(S)-2-[4-(3-Fluorobenzyloxy)benzyl]amino-N,N-dimethylpropionamide, methanesulfonate;
(S)-2-[4-(2-Chlorobenzyloxy)benzyl]amino-N,N-dimethylpropionamide, methanesulfonate;
(S)-2-[4-(2-Chlorobenzyloxy)benzyl]amino-3-hydroxy-N,N-dimethyl propionamide, methanesulfonate; and
(S)-2-(4-Benzyloxybenzyl)amino-N,N-dimethylpropionamide, methanesulfonate.

EXAMPLE 5

8 g (0.026 mol) of [4-(3-chlorobenzyl)oxybenzyl]aminoacetamide are dissolved in methanol (100 ml) and 3.6 g (0.029 mol) of anhydrous potassium carbonate are added to the solution. Methyl iodide (3 ml; 0.050 mol) is dropped into the mixture which is stirred for 2 hours at room temperature and then evaporated to dryness. The crude residue is chromatographed on silica gel(eluant: chloroform/methanol; 95/5). 4.25 g (51.3%) of 2-[N-(4-3-chlorobenzyloxy)benzyl)-N-methyl]aminoacetamide are obtained (m.p. 108°-111° C.).

Analogously the following compounds can be obtained and, if required, salified with a suitable acidic agent:
(S)-2-[N-(4-Benzyloxybenzyl)-N-methyl]amino-N-methyl propionamide; m.p. 80°-82.5° C.;
(S)-2-[N-(4-(3-Chlorobenzyloxy)benzyl)-N-methyl]amino-3-hydroxy-N-methylpropionamide, fumarate m.p. 87.5°-95° C. (dec);
(S)-2-[N-(4-Benzyloxybenzyl)-N-methyl]amino-3-hydroxy-N-methylpropionamide; m.p. 75°-78° C.;
(S)-2-[N-(4-(3-Chlorobenzyloxy)benzyl)-N-methyl]amino-N-methylpropionamide, oxalate m.p. 75°-85° C.(1.54% water);
(S)-N-[(4-Benzyloxybenzyl)-N-methyl]aminopropionamide m.p. 102°-104° C.; and
(S)-2-[N-(4-(3-Chlorobenzyloxy)benzyl)-N-methyl]aminopropionamide m.p. 81°-84° C.

EXAMPLE 6

Tablets, each weighing 300 mg and containing 100 mg of active substance can be manufactured as follows:

| Compositions (for 5000 tablets) | |
| --- | --- |
| [4-(3-Chlorobenzyl)oxybenzyl]aminoacetamide, hydrochloride | 500 g |
| Lactose | 710 g |
| Corn starch | 237.5 g |
| Talc powder | 37.5 g |
| Magnesium stearate | 15 g |

2-[4-(3-chlorobenzyloxy)benzyl]aminoacetamide hydrochloride, lactose and half of the corn starch are mixed; the mixture is then forced through a sieve of 0.5 mm openings. Corn starch (18 g) is suspended in warm water (180 ml).
The resulting paste is used to granulate the powder. The granules are dried, comminuted on a sieve of sieve size 1.4 mm, then the remaining quantity of starch, talc and magnesium is added, carefully mixed, and processed into tablets.

EXAMPLE 7

Tablets, each weighing 300 mg and containing 100 mg of the active substance can be manufactured as follows:

| Compositions (for 500 tablets) | |
| --- | --- |
| (S)-2-(4-Benzylbenzyl)aminopropionamide, methanesulfonate | 500 g |
| Lactose | 710 g |
| Corn starch | 237.5 g |
| Talc powder | 37.5 g |
| Magnesium stearate | 15 g |

(S)-2-(4-Benzylbenzyl)aminopropionamide methanesulfonate, lactose and half of the corn starch are mixed; the mixture is then forced through a sieve of 0.5 mm openings. Corn starch (18 g) is suspended in warm water (180 ml).
The resulting paste is used to granulate the powder. The granules are dried, comminuted on a sieve size 1.4 mm, then the remaining quantity of starch, talc and magnesium is added, carefully mixed, and processed into tablets.

We claim:
1. A compound of formula (Ia)

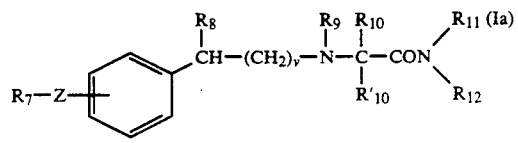

wherein
$R_7$ is $C_1$-$C_8$ alkyl; a $C_3$-$C_8$ cycloalkyl ring; or a phenyl ring unsubstituted or substituted by 1 to 4 substituents independently selected from the group consisting of halogen, $C_1$-$C_6$ alkyl, $C_1$-$C_6$ alkoxy and trifluoromethyl;

Z is a —$(CH_2)_r$— or —$(CH_2)_s$—Y—$(CH_2)_t$— group, wherein r is an integer of 1 to 4, one of s and t is zero and the other is zero or an integer of 1 to 4, and Y is —O—, —S— or —$NR_{13}$— in which $R_{13}$ is hydrogen or $C_1$-$C_4$ alkyl;

v is zero or 1;

each of $R_8$ and $R_9$, independently, is hydrogen or $C_1$-$C_4$ alkyl;

$R_{10}$ is hydrogen, $C_1$-$C_4$ alkyl unsubstituted or substituted by hydroxy or by a phenyl ring optionally substituted by 1 to 4 substituents independently selected from the group consisting of halogen, $C_1$-$C_6$ alkyl, $C_1$-$C_6$ alkoxy and trifluoromethyl;

$R'_{10}$ is hydrogen; or $R_{10}$ and $R'_{10}$ taken together with the adjacent carbon atom form a $C_3$-$C_6$ cycloalkyl ring;

each of $R_{11}$ and $R_{12}$, independently, is hydrogen or $C_1$-$C_6$ alkyl; and pharmaceutically acceptable salts thereof; and wherein a) when $R_7$ is $C_1$-$C_8$ alkyl, then Z is a —$(CH_2)_s$—Y—$(CH_2)_t$— group in which both of s and t are zero and Y is as defined above;

b) when $R_7$ is $C_1$-$C_8$ alkyl and, at the same time, Z is a —$(CH_2)_s$—Y—$(CH_2)_t$— group in which both of s and t are zero and Y is —O—, $R_{10}$ is hydrogen or $C_1$-$C_4$ alkyl, $R'_{10}$ is hydrogen, or $R_{10}$ and $R'_{10}$ taken together with the adjacent carbon atom form a $C_3$-$C_6$ cycloalkyl ring, and v, $R_9$, $R_{11}$ and $R_{12}$ are as defined above, then $R_8$ is $C_1$-$C_4$ alkyl;

c) when Z is a group —$(CH_2)_s$—Y—$(CH_2)_t$—, in which s, t and Y are as defined above, and at the same time $R_7$ is a phenyl ring unsubstituted or substituted by 1 or 2 substituents selected from the group consisting of halogen, $C_1$-$C_6$ alkyl, $C_1$-$C_6$ alkoxy and trifluoromethyl, $R_{10}$ is hydrogen or $C_1$-$C_4$ alkyl, $R'_{10}$ is hydrogen, and v, $R_8$ and $R_9$ are as defined above, then at least one of $R_{11}$ and $R_{12}$ is other than hydrogen;

d) when $R_7$ is phenyl unsubstituted or substituted by 1 to 4 substituents selected from the group consisting of halogen and $C_1$-$C_6$ alkyl, and at the same time Z is a —$CH(R_{14})$— or —$(CH_2)_s$—Y—$(CH_2)_t$— group, in which $R_{14}$ is hydrogen or $C_1$-$C_3$ alkyl, Y is —O— or —S— and s and t are both zero, $R_8$ and $R_9$ are hydrogen, v is zero and $R_{10}$, $R'_{10}$, $R_{11}$ and $R_{12}$ are as defined above, then $R_{10}$ is other than hydrogen or unsubstituted $C_1$-$C_4$ alkyl.

2. The compound of claim 1, wherein $R_7$ is a phenyl ring unsubstituted or substituted by one or two substituents independently selected from the group consisting of halogen, $C_1$-$C_4$ alkyl and trifluoromethyl;

Z is a —$(CH_2)_r$— or —$(CH_2)_s$—Y—$(CH_2)_t$ group, wherein r is 1 or 2, one of s and t is zero and the other is zero, 1 or 2, and Y is —O—, —S— or —NH—;

v is zero or 1;

each of $R_8$ and $R_9$, independently, is hydrogen or $C_1$-$C_4$ alkyl;

$R_{10}$ is hydrogen or $C_1$-$C_4$ alkyl optionally substituted by hydroxyl;

$R'_{10}$ is hydrogen;

each of $R_{11}$ and $R_{12}$ is independently hydrogen or $C_1$-$C_4$ alkyl; and wherein a) when Z is a group —$(CH_2)_s$—Y—$(CH_2)_t$, in which s, t and Y are as defined above, and at the same time $R_7$ is a phenyl ring as defined above, $R_{10}$ is hydrogen or unsubstituted $C_1$-$C_4$ alkyl, v, $R_8$ and $R_9$ are as defined above, then at least one of $R_{11}$ and $R_{12}$ is other than hydrogen;

b) when $R_7$ is a phenyl ring unsubstituted or substituted by one or two substituents selected from the group consisting of halogen and $C_1$-$C_4$ alkyl, and at the same time Z is a —$CH(R_{14})$— or —$(CH_2)_s$—Y—$(CH_2)_t$— group in which $R_{14}$ is hydrogen or $C_1$-$C_3$ alkyl, Y is —O— or —S— and s and t are both zero, $R_8$ and $R_9$ are hydrogen, v is zero and $R_{11}$ and $R_{12}$ are as defined above, then $R_{10}$ is $C_1$-$C_4$ alkyl substituted by hydroxy.

3. A compound of formula (Ib)

$$R'_7-Z'-\underset{}{\bigcirc}-\underset{R'_8}{\overset{}{C}H}-(CH_2)_w-\underset{R'_9}{\overset{}{N}}-\underset{R''_{10}}{\overset{}{C}H}-CON\underset{R'_{12}}{\overset{R'_{11}}{\diagup}} \quad (Ib)$$

wherein $R'_7$ is a phenyl ring unsubstituted or substituted by a halogen atom;

$Z'$ is a —$(CH_2)_r$— or —$(CH_2)_s$—Y—$(CH_2)_t$— group in which r is 1, one of s and t is zero and the other is zero or 1, and Y is —O—, —S— or —NH—;

$R'_8$ is hydrogen;

w is zero;

$R'_9$ is hydrogen or methyl;

$R''_{10}$ is hydrogen or methyl;

$R'_{11}$ and $R'_{12}$ are hydrogen; and the pharmaceutically acceptable salts thereof.

4. The compound of claim 1 selected from the group consisting of:

2-[4-(2-chlorobenzyloxy)benzyl]amino-3-hydroxy-N-methylpropionamide;

2-[4-(3-fluorobenzyloxy)benzyl]amino-3-hydroxy-N-methylpropionamide;

2-[4-(2-fluorobenzyloxy)benzyl]amino-3-hydroxy-N-methylpropionamide;

2-[N-(4-benzylbenzyl)-N-methyl]aminopropionamide;

2-[4-(3-chlorobenzyloxy)benzyl]amino-3-hydroxy-N-methylpropionamide;

2-(4-benzyloxybenzyl)amino-3-hydroxy-N-methylpropionamide;

2-[4-(3-chlorobenzyloxy)benzyl]amino-N-methylacetamide;

2-(4-phenyloxybenzyl)amino-3-hydroxy-N-methylpropionamide;

2-[4-(2-phenylethyl)benzyl]aminopropionamide;

2-[4-(2-chlorobenzyloxy)benzyl]amino-N-methylpropionamide;

2-(4-benzyloxybenzyl)amino-N-methylpropionamide;

as single (S) or (R) isomers and mixtures thereof and pharmaceutically acceptable salts thereof.

5. The compound of claim 3 selected from the group consisting of:

2-(4-benzyloxybenzyl)aminopropionamide;

2-[4-(2-chlorobenzyloxy)benzyl]aminopropionamide;

2-(4-benzylaminobenzyl)aminopropionamide;

2-[4-(3-fluorobenzyloxy)benzyl]aminopropionamide;

2-[4-(3-chlorobenzyloxy)benzyl]aminopropionamide;

2-[N-[4-(3-chlorobenzyloxy)benzyl]-N-methyl-]aminoacetamide;
2-(4-benzylbenzyl)aminopropionamide;
2-(4-phenyloxymethylbenzyl)aminopropionamide;
2-(4-benzylthiobenzyl))aminopropionamide; as single (S) or (R) isomers and mixtures thereof and pharmaceutically acceptable salts thereof.

6. A method for the treatment of a patient having epilepsy, comprising administering to said patient an effective amount of compound of formula (I)

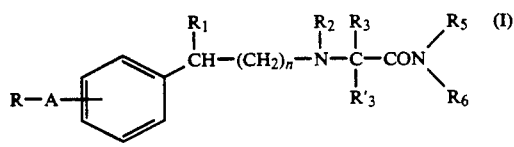

wherein
R is $C_1$-$C_8$ alkyl; a $C_3$-$C_8$ cycloalkyl ring; or a phenyl ring unsubstituted or substituted by 1 to 4 substituents independently selected from the group consisting of halogen, $C_1$-$C_6$ alkyl, $C_1$-$C_6$ alkoxy and trifluoromethyl;

A is a —$(CH_2)_m$— or —$(CH_2)_p$—X—$(CH_2)_q$— group, wherein m is an integer of 1 to 4, one of p and q is zero and the other is zero or an integer of 1 to 4, and X is —O—, —S— or —$NR_4$— in which $R_4$ is hydrogen or $C_1$-$C_4$ alkyl;

n is zero or 1;

each of $R_1$ and $R_2$, independently, is hydrogen or $C_1$-$C_4$ alkyl;

$R_3$ is hydrogen, $C_1$-$C_4$ alkyl unsubstituted or substituted by hydroxy or by a phenyl ring optionally substituted by 1 to 4 substituents independently selected from the group consisting of halogen, $C_1$-$C_6$ alkyl, $C_1$-$C_6$ alkoxy and trifluoromethyl;

$R'_3$ is hydrogen; or $R_3$ and $R'_3$ taken together with the adjacent carbon atom form a $C_3$-$C_6$ cycloalkyl ring;

each of $R_5$ and $R_6$, independently, is hydrogen or $C_1$-$C_6$ alkyl; and wherein when R is $C_1$-$C_8$ alkyl, then A is a —$(CH_2)_p$—X—$(CH_2)_q$— group in which p and q are both zero and X is as defined above; or a pharmaceutically acceptable salt thereof, and a pharmaceutically acceptable carrier.

7. The method of claim 6, wherein
R is a phenyl ring unsubstituted or substituted by one or two substituents independently selected from the group consisting of halogen, $C_1$-$C_4$ alkyl and trifluoromethyl;

A is a —$(CH_2)_m$— or —$(CH_2)_p$—X—$(CH_2)_q$— group, wherein m is 1 or 2, one of p and q is zero and the other is zero, 1 or 2, and X is —O—, —S— or —NH—;

n is zero or 1;

each of $R_1$ and $R_2$, independently is hydrogen or $C_1$-$C_4$ alkyl;

$R_3$ is hydrogen or $C_1$-$C_4$ alkyl optionally substituted by hydroxy;

$R'_3$ is hydrogen; and each of $R_5$ and $R_6$ is independently hydrogen or $C_1$-$C_4$ alkyl.

8. The method of claim 6, wherein
R is phenyl ring unsubstituted or substituted by halogen;

A is a —$(CH_2)_m$— or —$(CH_2)_p$—X—$(CH_2)_q$— group, wherein m is 1 or 2, one of p and q is zero and the other is zero or 1 and X is —O—, —S— or —NH—;

n is zero;

$R_1$ is hydrogen;

$R_2$ is hydrogen or $C_1$-$C_4$ alkyl;

$R_3$ is hydrogen or $C_1$-$C_2$ alkyl optionally substituted by hydroxy;

$R'_3$ is hydrogen;

each of $R_5$ and $R_6$ is independently is hydrogen or $C_1$-$C_4$ alkyl.

9. The method of claim 6, wherein said compound is selected from the group consisting of:
2-(4-benzyloxybenzyl)aminopropionamide;
2-[4-(2-chlorobenzyloxy)benzyl]amino-3-hydroxy-N-methylpropionamide;
2-[4-(2-chlorobenzyloxy)benzyl]aminopropionamide;
2-[4-(3-fluorobenzyloxy)benzyl]amino-3-hydroxy-N-methylpropionamide;
2-(4-benzylaminobenzyl)aminopropionamide;
2-[4-(3-fluorobenzyloxy)benzyl]aminopropionamide;
2-[4-(2-fluorobenzyloxy)benzyl]amino-3-hydroxy-N-methylpropionamide;
2-[N-(4-benzylbenzyl)-N-methyl]aminopropionamide;
2-[4-(3-chlorobenzyloxy)benzyl]amino-3-hydroxy-N-methylpropionamide;
2-(4-benzyloxybenzyl)amino-3-hydroxy-N-methylpropionamide;
2-[4-(3-chlorobenzyloxy)benzyl]aminopropionamide;
2-[N-[4-(3-chlorobenzyloxy)benzyl]-N-methyl-]aminoacetamide;
2-[4-(3-chlorobenzyloxy)benzyl]amino-N-methylacetamide;
2-(4-phenyloxybenzyl)amino-3-hydroxy-N-methylpropionamide;
2-(4-benzylbenzyl)aminopropionamide;
2-[4-(2-phenylethyl)benzyl]aminopropionamide;
2-[4-phenyloxymethylbenzyl)aminopropionamide;
2-(4-benzylthiobenzyl)aminopropionamide;
2-[4-(2-chlorobenzyloxy)benzyl]amino-N-methylpropionamide;
2-(4-benzyloxybenzyl)amino-N-methylpropionamide; and
2-[4-(3-chlorobenzyloxy)benzyl]aminoacetamide,
as single (S) or (R) isomers and mixtures thereof.

10. A pharmaceutical composition comprising a pharmaceutically acceptable carrier or diluent and an effective amount of the compound of formula (Ia) of claim 1 or a pharmaceutically acceptable salt thereof.

11. A pharmaceutical composition comprising a pharmaceutically acceptable carrier or diluent and an effective amount of the compound of formula (Ib) of claim 3 or a pharmaceutically acceptable salt thereof.

12. The compound of 2-[4-(3-phenylpropyl)oxybenzyl] aminopropionamide or a pharmaceutically acceptable salt thereof.

13. A pharmaceutical composition comprising a suitable carrier and/or diluent and, as an active principle, the compound according to claim 12 or a pharmaceutically acceptable salt thereof.

14. A method for the treatment of a patient having epilepsy, which method comprises administering to the patient an effective amount of the compound as defined in claim 12 or as a pharmaceutically acceptable salt thereof.

15. A method for the treatment of a patient having epilepsy, which comprises administering to the patient an effective amount of a pharmaceutical composition as defined in claim 13.

* * * * *